(12) United States Patent
Cipriani et al.

(10) Patent No.: US 6,841,669 B2
(45) Date of Patent: Jan. 11, 2005

(54) FUNCTIONALIZED THIOPHENE OLIGOMERS AND THEIR USE AS FLUORESCENT MARKERS

(75) Inventors: Franco Cipriani, Turi (IT); Giuseppe Gigli, Rome (IT); Roberto Cingolani, Lecce (IT); Laura Favaretto, Ozzano Dell'Emilia (IT); Massimo Zambianchi, Cesena (IT); Giovanna Sotgiu, Bologna (IT); Giovanna Barbarella, Bologna (IT); Gennaro Citro, Rome (IT)

(73) Assignees: Consiglio Nazionale delle Ricerche, Rome (IT); Istituto Nazionale per la Fisica Della Materi, Genoa (IT); Bio-D S.r.l., Valenzano (IT)

( * ) Notice: Subject to any disclaimer, the term of this patent is extended or adjusted under 35 U.S.C. 154(b) by 57 days.

(21) Appl. No.: 09/871,353

(22) Filed: May 30, 2001

(65) Prior Publication Data

US 2002/0086437 A1 Jul. 4, 2002

(30) Foreign Application Priority Data

May 31, 2000 (IT) .................................... BA2000A0020

(51) Int. Cl.$^7$ ...................... C07D 413/06; G01N 21/76
(52) U.S. Cl. ............................ 544/146; 549/1; 549/29; 549/68; 436/164; 436/172; 435/4; 435/7.1
(58) Field of Search .............................. 435/4, 7.1, 174, 435/180; 424/181.1, 179.1, 1.53; 544/146; 549/1, 29, 68; 436/164, 172

(56) References Cited

U.S. PATENT DOCUMENTS 5,869,051 A * 2/1999 Roncucci et al. ......... 424/181.1
5,942,387 A * 8/1999 Hollinshead ................... 435/5
6,005,113 A 12/1999 Wu et al.
6,136,984 A * 10/2000 D.o slashed.rwald .......... 549/1
6,150,536 A 11/2000 Chondroudis et al.

OTHER PUBLICATIONS

Berlin et al., Adsorption of Carboxyl–Terminated Dithiophene and terthiophene Molecules on ITO Electrodes and their Electrochemical Coupling to Polymer Layers. The Influence of Molecular Geometry, 1998, JACS, 120(51):13453–13460.*

"The Synthesis and Examination of Some Fluorescent Derivatives of 2,2'—Bithienyl and 2-(2'–Furyl)–thiopen", by R.E. Atkinson and F.E. Hardy, pp. 357–361.

"Qsar Evaluation of Oc–Terthienyl Phototoxicity", by Gilman D. Veith, Ovanes G. Mekenyan, Gerald T. Ankley, and Daniel J. Call, 1995, pp. 1267–1272.

"Design, Structure, and Optical Properties of Organic—Inorganic Perovskites Containing an Oligothiophene Chromophore", by David B. Mitzi, KonstantinosChondroudis, and Cherie R. Kagan, Aug. 31, 1999, pp. 6246–6256.

* cited by examiner

Primary Examiner—Padmashri Ponnaluri
Assistant Examiner—My-Chau T Tran
(74) Attorney, Agent, or Firm—David A. Farah; Sheldon & Mak

(57) ABSTRACT

Thiophene oligomers which are excitable in the visible and ultraviolet region and each having at least one functional group able to form a covalent bond with organic and/or biological molecules, so as not to alter either the fluorescence properties of the oligomers or the biological activity of the bound molecules, and their use as fluorescent markers in analysis techniques.

9 Claims, 3 Drawing Sheets

FUNCTIONALIZED THIOPHENE OLIGOMERS AND THEIR USE AS FLUORESCENT MARKERS

CROSS-REFERENCE TO RELATED APPLICATION

This application claims priority from Italian Patent Application BA2000A000020 titled "Oligomeri Del Tiofene Funzionalizzati E Loro Utilizzo Come Marcatori Fluorescenti," filed May 31, 2000; the contents of which are incorporated by reference herein in its entirety.

FIELD OF THE INVENTION

The present invention concerns thiophene oligomers having suitable functionalization groups, which allow the same oligomers to covalently bind themselves to organic and/or biological molecules as well as to be used as fluorescent markers in analysis techniques.

BACKGROUND

In recent years labeling techniques with fluorescent compounds have replaced the radioisotope based ones as analytical tools in biomedical applications.

Fluorescent markers allow the highly sensitive and precise measurement of components of complex biological systems and are nowadays widely used in the biological, pharmacological and medical field.

Fluorescence is the most suitable analytical tool for monitoring antigen-antibody interactions in many bioanalytical, immunochemical and histological applications, for labeling nucleic acids etc.

Several families of differently colored fluorescent markers are currently available on the market. Some of these are high molecular weight compounds, others are low molecular weight compounds with a greater capacity of penetrating the cellular membrane, others, lastly, are complex systems in which the light is emitted through a complex set of intermolecular interactions. (Handbook of Fluorescent Probes and Research Chemicals, Seventh Edition; Molecular Probes Inc., Eugene, Oreg., 1999; Fluorescent and Luminescent Probes for Biological Activity. A Practical Guide to Technology for Quantitative Real-Time Analysis, Second Edition, W. T. Mason, ed. Academic Press, 1999).

Each different family of markers requires a different chemical methodology for the bond formation between the marker and biological molecule.

Therefore, there is a need for a family of fluorescent markers in all colors of visible and possessing the same chemical characteristics, so as to be able to apply the same standard methodology for labeling in all the colors. One such family of markers would considerably help the experiments in the biomedical field, and particularly the experiments for the simultaneous monitoring of different biochemical reactions and species.

Additionally, there is a need for a class of fluorescent markers with high absorbance values, wide differences between absorption and emission frequencies and high quantum yields of photoluminescence (the ratio between the number of photons emitted and those absorbed).

Thiophene oligomers have been extensively studied in recent years due to their optic properties. In particular, thiophene oligomers have high absorbance values and broad differences between absorption and emission frequencies (H. S. Nalwa, Ed. Handbook of organic conductive molecules and polymers, John Wiley & Sons. Chichester, 1997, Vol. 1–4; Electronic Materials: The Oligomer Approach. K. Müllen, G. Wegner, Eds. Wiley-VCH, New York, 1998; Handbook of oligo and polythiophenes, D. Fichou, Ed. Wiley-VCH. New York, 1999).

Besides, it has been shown that thiophene oligomers can reach very high quantum yields of photoluminescence, both in solution as well as the solid state and that, through molecular engineering, their fluorescence frequency can be modulated in the entire spectrum of visible and the nearby IR (Oligothiophene-S, S-dioxides. Synthesis and electronic properties in relation to the parent oligothiophenes, G. Barbarella, et al. J. Org. Chem. 1998, 63, 5497–5506; High-efficiency oligothiophene-based light-emitting diodes G. Gigli, et al. Appl. Phys. Lett. 1999, 75, 439–441; Color engineering by modified oligothiophene blends, M. Anni, et al. Appl. Phys. Lett. 2000, 77, 2458–2460; Molecular packing and photoluminescence efficiency in odd-membered oligothiophene-S, S-dioxides, L. Antolini, et al. J. Am. Chem. Soc. 2000, 122, 9006–9013; Tuning solid-state photoluminescence frequencies and efficiencies of oligomers containing one central thiophene-S, S-dioxide unit G. Barbarella, et al. J. Am. Chem. Soc. 2000, 122, 11971–11978; Multicolor oligothiophene-based LEDs G. Gigli, et al. Appl. Phys. Lett. 2001, 78, 1493–1495).

Finally, it has been shown that, with suitable functionalizations, these oligomers can be made soluble not only in organic solvents but also in water (Polyhydroxyl Oligothiophenes. I. Regioselective Synthesis of 3,4'- and 3,3'-di (2-hydroxyethyl) 2,2'-bithiophene via Palladium Catalyzed Coupling of Thienylstannanes with Thienylbromides, G. Barbarella, M. Zambianchi. Tetrahedron 1994, 50, 11249–11256).

SUMMARY

The inventors of the present invention have found that thiophene oligomers can be functionalized in a suitable way such as to bind themselves to the biological molecules through a covalent bond, without this altering either the fluorescence properties of the oligomers or the biological activity of the bound molecules.

The subject of the present invention are thiophene oligomers with each having at least one functional group able to form a covalent bond with organic molecules or biological molecules or both, and excitable in the region of visible and ultraviolet light.

Such oligomers have between 2 and 5 thiophene rings, preferably between 3 and 4.

The functional groups used are selected from the group consisting of NH2, CHO, COOH, SH and NCS. Preferably the functional group is NCS.

The functional group NCS can be bound to the oligomer by means of an alkyl spacer R including from 2 to 4 carbon atoms. Preferably the alkyl spacer is $CH_2CH_2$— or $(CH_3)_2Si$—$CH_2$—.

An additional object of the present invention is the use of the thiophene oligomers described above as fluorescent markers.

In particular, the oligomers of the present invention are used as fluorescent markers for organic molecules or biological molecules or both. Preferably, the oligomers of the present invention are used as fluorescent markers for proteins, polyclonal antibodies or monoclonal antibodies or both, and their fractions, nucleic acids, oligonucleotides, hormones, medicines, drugs, and non-proteic chemical neurotransmitters.

Preferably the oligomers of the present invention are used as fluorescent markers in spectrometry, spectrofluorimetry, flow and static cytometry, fluorescence microscopy and gel electrophoresis.

Finally, an additional object of the present invention is a conjugate of a thiophene oligomer as defined above with an organic or biological molecule. Here and afterwards, conjugate means a compound made up of a thiophene oligomer covalently bound to an organic or biological molecule.

FIGURES

These and other features, aspects and advantages of the present invention will become better understood with regard to the following description, appended claims, and accompanying figures where:

Figure 5:
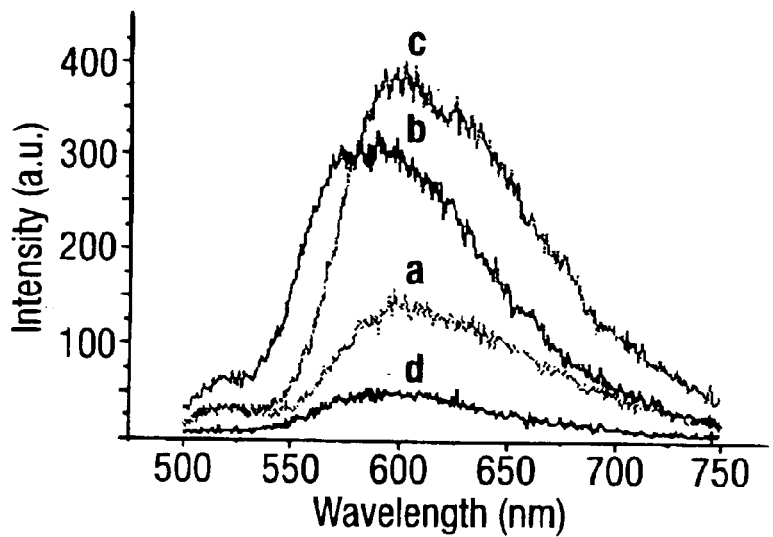
Figure 6:
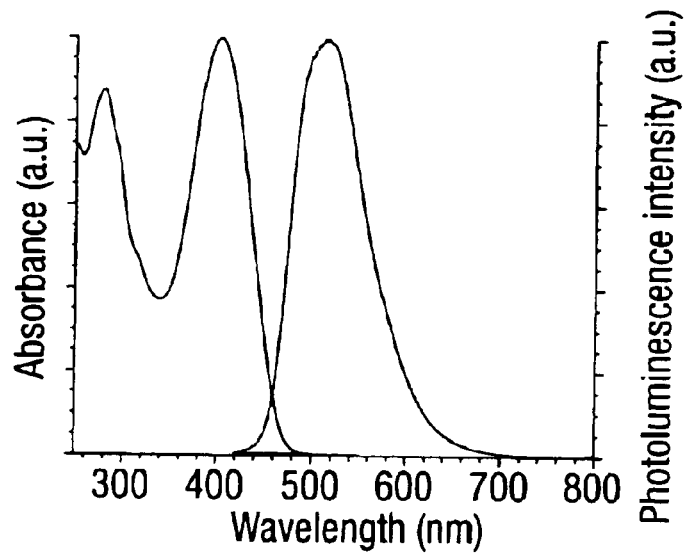

FIG. 5 shows some photoluminescence spectra ($\lambda_{exc.}$=488 nm) of a conjugate of the isothiocyanate 4 thiophene oligomer with the anti-CD8 antibody for different values of the molar ratio 4:anti-CD8; and FIG. 6 shows some normalized and emission spectra of the isothiocyanate 5 thiophene oligomer in methylene chloride.

DESCRIPTION

EXAMPLE 1

Preparation of Thiophene Oligomers 1–4

This example outlines the preparation procedure of some isothiocyanate (oligomers 1–4) thiophene oligomers in which the NCS group is inserted in the oligomer through the $CH_2CH_2$— spacer or the $(CH_3)_2Si$—$CH_2$— spacer. The spacer allows the fluorescent oligomer to be kept a sufficient distance from the protein (or molecule of biological interest) so as not to affect the biological activity of the same and, at the same time, not change the fluorescence properties of the oligomer.

As will be easily comprehensible to a person skilled in the art, the preparation of these oligomers entailed the use of all known reactions and hence is not described in detail.

Diagram 1 (Preparation of Thiophene Oligomers 1–4)

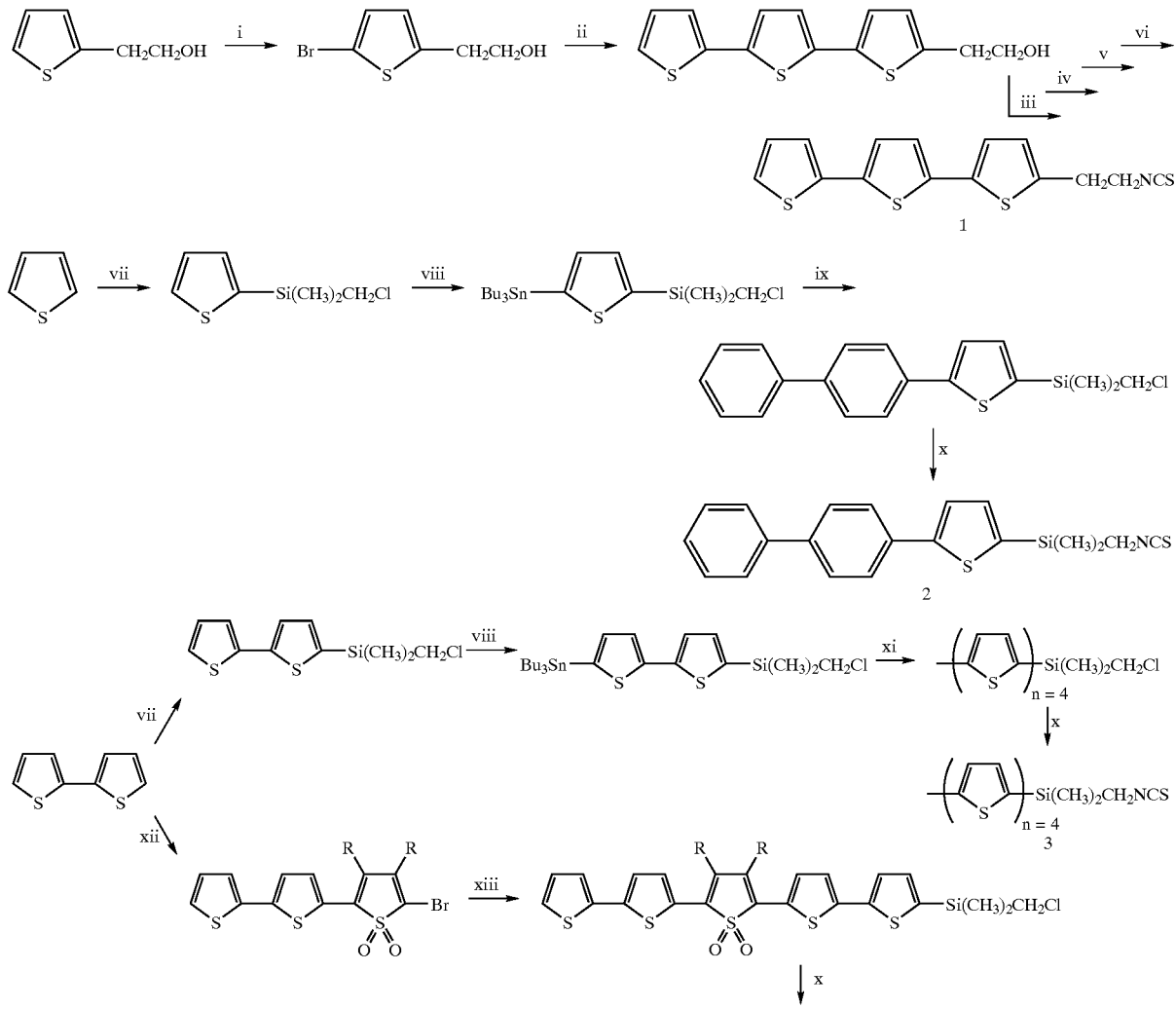

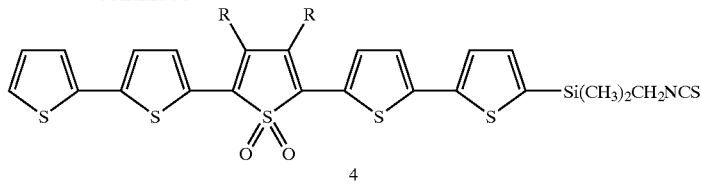

4

Diagram 1: i) NBS, toluene, −20° C. ii) 2-tributylstannylthiophene, Pd(ASPh₃)₄, toluene, 110° C. iii) CH₃SO₂Cl, CH₂Cl₂, Et₃N, −20° C. iv)NaN₃, DMF, 60° C. V)LiAlH₄, Et₂O. vi) 2-pyridyl thiocarbonate, CH₂Cl₂. vii) LDA,ClCH₂Me₂SiCl. viii) BuLi, Bu₃SnCl. ix) 4-biphenylbromide, Pd(AsPh₃)₄, toluene, 110° C. x) NaSCN, acetone, Et₂O. xi) 5-bromo-2,2'-bithiophene, Pd(AsPh₃)₄, toluene, 110° C. xii) 2,5-dibromo-3,4-dihexyl-thiophene-1,1-dioxide, Pd(AsPh₃)₄, toluene, 110° C. xiii) 5-[dimethyl(chloromethyl)silyl]-5'-tributylstannyl-2,2'-bithiophene, Pd(AsPh₃)₄, toluene, 110° C.

Diagram 2 (Preparation of Thiophene Oligomer 5)

TABLE 1-continued

| thiophene oligomers | λmax[a] | ε[c] | λPL[a,b] | Δ(λPL-λmax) |
|---|---|---|---|---|
| 3 | 396 | 47000 | 560 | 164 |
| 4 | 477 | 38000 | 650 | 173 |

[a]in nm, in CH₂Cl₂;
[b]λexc. = 325 nm;
[c]cm⁻¹M⁻¹

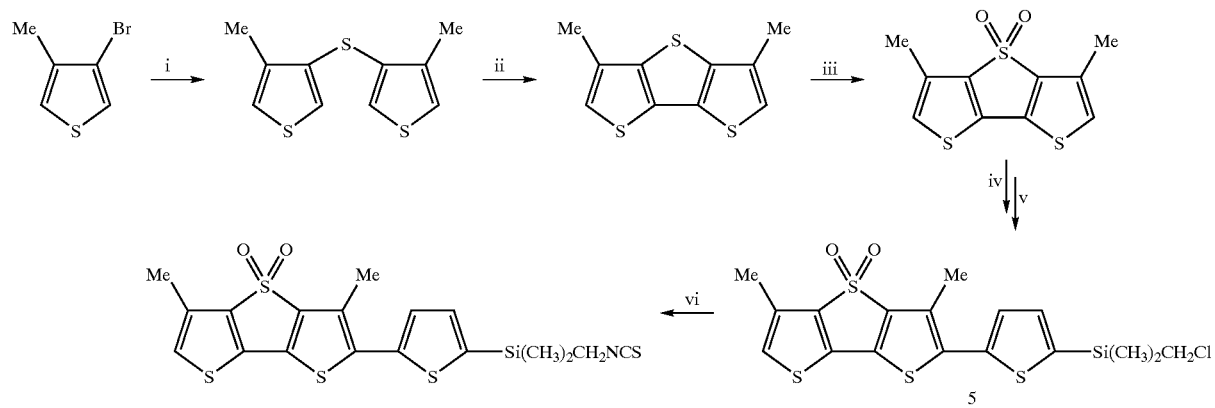

Diagram 2: i) BuLi/Et2O, (PhSO2)2S. ii) BuLi/Et2O, CuCl2. iii) Acetic acid, H2O2. iv) NBS, DMF. v) 5-[dimethyl (chloromethyl) silyl]5-tributylstannyl-thiophene, Pd (AsPh3) 4, toluene, 110° C. vi) NaSCN, acetone, Et2O.

EXAMPLE 2

Photoluminescence Tests of the Thiophene Oligomers

For each oligomer, the synthesis of which is described in the previous example, the wavelengths of absorption maxima (λmax) and of emission (λPL, under excitation with ultraviolet light), the absorbance values (ε) and the differences Δ (λPL-λmax) were all measured and are shown in Table 1.

TABLE 1

| thiophene oligomers | λmax[a] | ε[c] | λPL[a,b] | Δ(λPL-λmax) |
|---|---|---|---|---|
| 1 | 360 | 18950 | 438 | 78 |
| 2 | 312 | 42000 | 450 | 138 |

Table 1 shows that the fluorescence covers the visible spectrum from blue to red also with just the four oligoiners shown.

EXAMPLE 3

Photoluminescence Tests of the Thiophene Oligomer Conjugates

The isothiocyanate thiophene oligomers were coupled according to standard methods with proteins.

The conjugates of the isothiocyanate thiophene oligomers with proteins showed the characteristics required for use of the same oligomers as markers for the qualitative and quantitative analysis of biological molecules.

FIGS. 1–4 show the fluorescence characteristics of the oligomer 1 conjugate with bovine serum albumin, BSA, V fraction.

The 1-BSA conjugate was obtained by separately dissolving BSA in 0.1-M sodium carbonate (pH 9.0) and the oligomer 1 in dimethyl sulphoxide in the desired concentrations and then mixing the two solutions in fixed molar ratios. The conjugate 1-BSA was separated by gel filtration in phosphate buffer (pH 7.2) after several hours.

Figure 1:
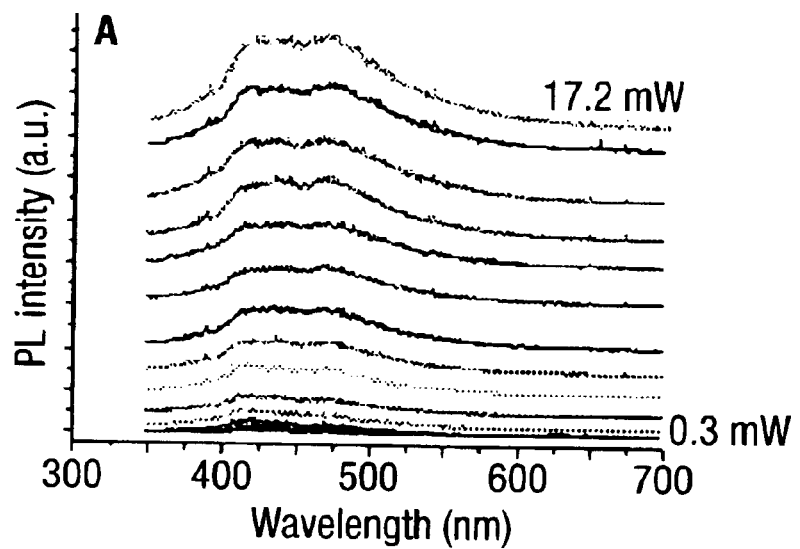
FIG. 1 shows a photoluminescence spectrum ($\lambda_{exc.}$=325 nm) of a conjugate of the isothiocyanate 1 thiophene oligomer with bovine serum albumin (BSA, V fraction) as a function of the power irradiated.
Figure 2:
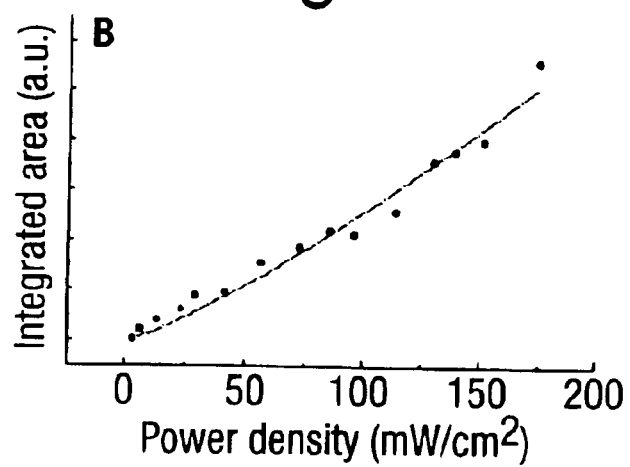
FIG. 2 is a graph that shows the integrated areas of the spectrum of FIG. 1.

FIG. 1 shows the fluorescence spectrum, under UV excitation, of the 1-BSA conjugate for different values of excitation power, while FIG. 2 shows the integrated area of the same spectra, from which it can be seen how the intensity of the fluorescence spectra increases with an increase in the excitation intensity.

Figure 3:
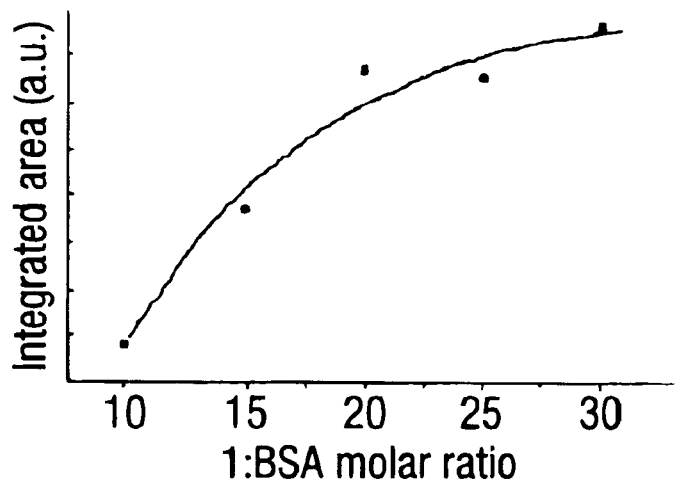
FIG. 3 is a graph which shows the integrated areas of the photoluminescence spectra ($\lambda_{exc.}$=325 nm) of a conjugate of the isothiocyanate 1 thiophene oligomer with bovine serum albumin as a function of the molar ratio (1:BSA)

FIG. 3 shows the integrated area of the fluorescence spectra of the conjugate 1-BSA as a function of the molar ratio of the components, from which it is seen that the intensity of the spectra increases with an increase in the number of oligomer 1 molecules bound to the protein.

Figure 4:
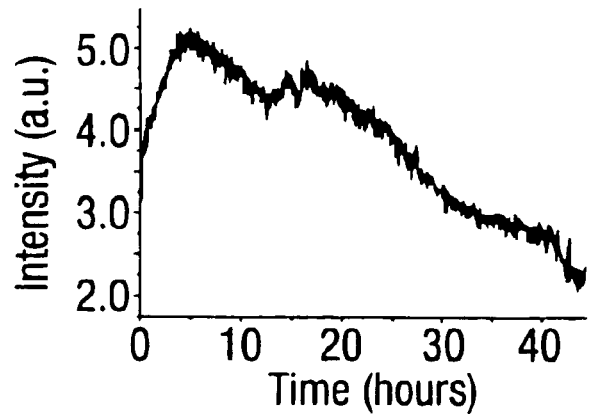
FIG. 4 is a graph which shows the variation as a function of the time of maximum intensity of the photoluminescence spectrum of the conjugate 1/BSA under continuous irradiation ($\lambda_{exc.}$=325 nm)

FIG. 4 shows the variation as a function of the time of the maximum intensity of the fluorescence spectrum of the 1-BSA conjugate under continuous ultraviolet light irradiation.

The Figure shows how, after almost two days of non-stop irradiation, the fluorescence spectrum of the conjugate still has an intensity of the order of half that of the initial spectrum. This shows the strong chemical stability and solidity of the optic properties of the 1-BSA conjugate.

FIG. 5 shows the fluorescence spectrum (under irradiation in visible, with $\lambda exc.=488$ nm) of the oligomer 4 conjugate with the monoclonal anti-CD8 antibody as a function of the molar ratio of the components.

The 4-(anti-CD8) conjugate was prepared using standard methods, first dialyzing the antibody in phosphate buffer (pH 7.4) vs. a carbonate buffer (pH 9.5) containing a non ionic detergent; then adding a solution of oligomer 4 in dimethyl sulphoxide so as to obtain the desired molar ratio of isothiocyanate-antibody and, finally, performing desalting chromatography on a GH25 column in phosphate buffer.

In FIG. 5 the spectra a), b) and c) are relative to oligomer:antibody molar ratios of 5:1, 10:1, 25:1. Spectrum d) is that of just the oligomer 4 in a concentration comparable with that of spectrum a) of the 4-(anti-CD8) conjugate.

The Figure shows that the intensity of the fluorescence spectrum of 4-(anti-CD8) conjugate increases with an increase in the oligomer:antibody molar ratio.

The Figure also shows that the intensity of the fluorescence spectrum of the conjugate is greater than the intensity of the fluorescence spectrum of the oligomer alone and that therefore the coupling does not result in the extinction of the fluorescence of the isothiocyanate thiophene oligomer.

The 4-(anti-CD8) conjugates were tested using flow cytometry to verify the activity of the labeled antibody as regards its specific antigen present on the surface of T-type lymphocytic cells. The activity of the labeled antibody proved to have been completely preserved.

The oligomer/protein solutions described above were systematically tested for a period exceeding three months. No variations in the properties nor precipitate formation were observed.

As for the photoluminescence quantum yields of the isothiocyanate thiophene oligomers (number of electrons emitted in the form of light as regards those absorbed), there are numerous publications which detail the way to check such yields by appropriately engineering the aforethe oligomers (Oligothiophene-S, S-dioxides. Synthesis and electronic properties in relation to the parent oligothiophenes, G. Barbarella, et al. J. Org. Chem. 1998, 63, 5497–5506; High-efficiency oligothiophene-based light-emitting diodes G. Gigli, et al. Appl. Phys. Lett. 1999, 75, 439–441; Color engineering by modified oligothiophene blends, M. Anni, et al. Appl. Phys. Lett. 2000, 77, 2458–2460; Molecular packing and photoluminescence efficiency in odd-membered oligothiophene-S, S-dioxides, L. Antolini, et al. J. Am. Chem. Soc. 2000, 122, 9006–9013; Tuning solid-state photoluminescence frequencies and efficiencies of oligomers containing one central thiophene-S, S-dioxide unit G. Barbarella, et al. J. Am. Chem. Soc. 2000, 122, 11971–11978; Multicolor oligothiophene-based LEDs G. Gigli, et al. Appl. Phys. Lett. 2001, 78, 1493–1495; Polyhydroxyl Oligothiophenes. I. Regioselective Synthesis of 3,4'- and 3,3'-di(2-hydroxyethyl) 2,2'-bithiophene via Palladium Catalyzed Coupling of Thienylstannanes with Thienylbromides, G. Barbarella, M. Zambianchi. Tetrahedron 1994, 50, 11249–11256). In particular, the higher values (0.6–0.8) are relative to oligomers containing a thienyl-S,S-dioxide group rigidly secured to two thiophene rings. With regard to this, the inventors prepared an isothiocyanate thiophene oligomer of this type (oligomer 5).

FIG. 6 shows the normalized absorption and emission spectra of oligomer 5, together with the absorbance and quantum yield values of photoluminescence of this isothiocyanate thiophene oligomer in methylene chloride.

As can be ascertained from the examples and figures above, the thiophene oligomers, subject of the present invention, offer numerous advantages when used as fluorescent markers. In fact, by making small changes to the molecular structure, it is possible to obtain a wide color variation of the fluorescence from visible to the nearby infrared. Besides, it should be emphasized how the same chemical nature for all the markers, aside from the fluorescence color, allows the standardization of the functionalization procedures, differently from conventional fluorescent markers which require a specific chemistry to be developed case by case.

Additional advantages offered by the use of thiophene oligomers as fluorescent markers concern the possibility of simultaneously exciting more markers by using just one ultraviolet and visible source, high chemical and optic stability of the same markers, high fluorescence efficiency and increased absorbance, the possibility of measuring different chemical species, in parallel and simultaneously, by means of functionalized markers, and a low molecular weight that allows high labeling ratios without causing steric obstruction and/or labeling problems of intracellular and intranuclear structures.

Although the present invention has been discussed in considerable detail with reference to certain preferred embodiments, other embodiments are possible. Therefore, the scope of the appended claims should not be limited to the description of preferred embodiments contained in this disclosure.

What is claimed is:

1. A thiophene oligomer, characterized in that it has at least one functional group able to form a covalent bond with a biological molecule and is excitable in the visible and ultraviolet light region without altering the biological activity of the biological molecule;

where the functional group is NCS;

where the NCS is bound to the oligomer by means of an alkyl spacer comprising from 2 to 4 carbon atoms;

where the thiophene oligomer has an outer thiophene ring; and where the NCS is attached in the α position to the outer thiophene ring.

2. A thiophene oligomer according to claim 1, where the alkyl spacer is selected from the group consisting of $CH_2CH_2$— and $(CH_3)_2Si$—$CH_2$—.

3. A thiophene oligomer excitable in the visible and ultraviolet light region comprising at least one functional NCS group able to form a covalent bond with one or more than one organic molecule, biological molecule or both;

where the NCS is bound to the oligomer by means of an alkyl spacer comprising from 2 to 4 carbon atoms;

where the thiophene oligomers have an outer thiophene ring; and where the thiophene oligomer has an outer thiophene ring; and where the NCS is attached in the α position to the outer thiophene ring.

4. A thiophene oligomer according to claim 3, where the alkyl spacer is selected from the group consisting of $CH_2CH_2$— and $(CH_3)_2Si$—$CH_2$—.

5. A method of detecting one or more than one molecule comprising:
 a) providing a thiophene oligomer according to claim 3,
 b) covalently bonding the thiophene oligomer to the one or more than one molecule; and
 c) detecting fluorescence of the bound thiophene oligomer.

6. The method of claim 5, where the one or more than one molecule is selected from the group consisting of proteins, polyclonal antibodies, fractions of polyclonal antibodies, monoclonal antibodies, fractions of monoclonal antibodies, nucleic acids, oligonucleotides, hormones, medicines, drugs, and non-proteic chemical neurotransmitters.

7. The method of claim 5, where detecting fluorescence comprises performing one or more than one procedure selected from the group consisting of spectrometry, spectrofluorimetry, flow and static cytometry, fluorescence microscopy and gel electrophoresis.

8. The method of claim 5, where the thiophene oligomer provided comprises a plurality of thiophene oligomers with different emission frequencies, and where detecting fluorescence comprises simultaneously exciting the thiophene oligomers, through one or more than one emissive radiation source.

9. A conjugate comprising a thiophene oligomer according to claim 3 covalently bound to an organic molecule or to a biological molecule.

* * * * *

UNITED STATES PATENT AND TRADEMARK OFFICE
CERTIFICATE OF CORRECTION

PATENT NO.    : 6,841,669 B2
DATED         : January 11, 2005
INVENTOR(S)   : Franco Cipriani et al.

It is certified that error appears in the above-identified patent and that said Letters Patent is hereby corrected as shown below:

Title page,
Item [73], Assignees, replace "Istituto Nazionale per la Fisica Della Materi" with -- Istituto Nazionale per la Fisica Della Materia --.

Signed and Sealed this

Fourteenth Day of February, 2006

JON W. DUDAS
*Director of the United States Patent and Trademark Office*